United States Patent

Simán

[11] Patent Number: 5,795,326
[45] Date of Patent: Aug. 18, 1998

[54] DOUBLE LUMEN TUBING DESIGN FOR CATHETER

[75] Inventor: Jaime E. Simán, Santa Ana, Calif.

[73] Assignee: Baxter International Inc., Deerfield, Ill.

[21] Appl. No.: 791,079

[22] Filed: Jan. 29, 1997

[51] Int. Cl.$^6$ .................................................. A61M 5/00
[52] U.S. Cl. .......................... 604/43; 604/264; 604/280
[58] Field of Search ..................... 604/43, 28, 52–54, 604/264, 272, 280, 283, 284

[56] References Cited

U.S. PATENT DOCUMENTS

| | | | |
|---|---|---|---|
| 4,568,329 | 2/1986 | Markurkar | 604/43 |
| 4,619,643 | 10/1986 | Bai | 604/43 |
| 4,643,711 | 2/1987 | Bates | 604/4 |
| 4,682,978 | 7/1987 | Martin | 604/43 |
| 4,772,268 | 9/1988 | Bates | 604/174 |
| 4,776,841 | 10/1988 | Catalano | 604/43 |
| 5,053,023 | 10/1991 | Martin | 604/280 |
| 5,106,368 | 4/1992 | Uldall | 604/43 |
| 5,156,592 | 10/1992 | Martin | 604/43 |
| 5,217,482 | 6/1993 | Keith | 606/194 |
| 5,364,376 | 11/1994 | Horzewski | 604/280 |
| 5,380,276 | 1/1995 | Miller | 604/28 |
| 5,397,302 | 3/1995 | Weaver | 604/54 |
| 5,425,714 | 6/1995 | Johnson | 604/102 |
| 5,480,380 | 1/1996 | Martin | 604/43 |

FOREIGN PATENT DOCUMENTS

| | | |
|---|---|---|
| 333308B1 | 1/1989 | European Pat. Off. . |
| 370158 | 1/1989 | European Pat. Off. . |
| 495263B1 | 12/1991 | European Pat. Off. . |
| 521430 | 6/1992 | European Pat. Off. . |
| WO89/09633 | 10/1989 | WIPO . |
| WO94/27666 | 12/1994 | WIPO . |
| WO96/00100 | 1/1996 | WIPO . |

Primary Examiner—John D. Yasko
Attorney, Agent, or Firm—Guy L. Cumberbatch; Bruce M. Canter; David J. Oldenkamp

[57] ABSTRACT

A double lumen tubing which is adapted for use as a catheter. Both lumens of the double lumen tubing have equal cross-sectional areas to provide equivalent flow volumes through each lumen. The lumen wall which divides the outer tubular wall into the two lumens has a central arcuate portion which is shaped to allow insertion of relatively large guidewires through the lumen while at the same time maintaining equivalent cross-sectional areas for each lumen. Resistance to kinking is increased by varying external diameters of each lumen to increase the wall thickness of the tubing in selected areas and by varying the thickness of the wall that divides both lumens at the two joints where the wall meets the tubular wall.

16 Claims, 2 Drawing Sheets

DOUBLE LUMEN TUBING DESIGN FOR CATHETER

BACKGROUND OF THE INVENTION

1. Field of the Invention

The present invention relates generally to medical devices which are used to provide access into the human body. More particularly, the present invention is directed to double lumen catheters which are used to provide infusion and/or removal of fluids from the body.

2. Description of Related Art

Central venous catheters are relatively long tubular devices which have tapered distal tips which are designed for entry into central veins to provide a dedicated route of fluid infusion into the body. The original venous catheters were single lumen devices which provided the ability to infuse a single liquid into the vein at one time. Multiple lumen catheters have since been developed which allow simultaneous introduction of two or more liquids into the vein. The dual lumen catheter is a common design which has been widely used for a number of years.

Dual lumen catheters include a tubular wall which forms a fluid conduit which typically has a circular cross-section. A single divider or lumen wall is formed inside the tubular wall to divide the circular fluid conduit into two lumens. In many instances, it is desirable that the two lumens have cross-sectional areas which are substantially equal. For example, equal lumen size is desirable in situations where the ability to provide two conduits with maximized fluid delivery rates on both lines is important.

Guidewires are commonly used to insert and locate catheters within the vascular system. The distal end of the guide wire is typically inserted into the vascular system and moved to the desired location for the catheter. The distal end of the catheter is then slipped over the guide wire and the catheter inserted into position as guided by the wire. Once the catheter is in position, the guide wire is withdrawn. It is important that the dual lumen catheter be designed to accommodate the use of guide wires. Some dual lumen catheters have included a separate lumen which is specifically designed to receive the guide wire while others have utilized one or both of the two fluid lumens as a temporary guide wire lumen. An advantage of designing and using one specific fluid lumen to receive the guide wire is that the overall size of the dual lumen catheter is minimized. This reduces the size of the wound made during insertion of the catheter into the body and reduces the wound healing time.

An important consideration in designing dual lumen catheters is to make the catheter as kink resistant as possible. In the past, kinking of the catheter during insertion into the body has been a significant problem. Accordingly, it is desirable that the cross-sectional configuration and other design features be chosen to maximize resistance to catheter kinking.

The currently available dual lumen catheters are adequate for their intended purpose. However, there is a continuing need to develop better dual lumen designs. For example, there is a continuing need to provide dual lumen catheters where the cross-sectional areas, i.e. size, of the lumens is kept the same while at the same time the kink resistance and guide wire compatibility of the dual lumen catheter are improved.

SUMMARY OF THE INVENTION

In accordance with the present invention, a dual lumen tubing is provided which is specifically designed for use as a catheter wherein the cross-sectional areas of the two lumens are substantially equal. The cross-sectional design of the dual lumen catheter is such that the size of the lumens are kept the same while the ability of the catheter to receive multiple size guidewires is increased. In addition, the catheter cross-sectional design provides for increased kink resistance.

The dual lumen tubing which is designed for use as a catheter includes a tubular wall which has an exterior surface and an interior surface. The tubular wall has a circular cross-section and is located about a longitudinal central axis. The interior surface of the tubular wall is divided into a first lumen portion located along a first lumen radius measured from the longitudinal central axis, and a second lumen portion located along a second lumen radius which is also measured from the longitudinal central axis. As a feature of the present invention, a lumen wall extends parallel to the longitudinal central axis and also extends transversely across the tubular conduit defined by the tubular wall. The lumen wall includes a first surface which, when combined with the first lumen portion of the interior surface forms a first lumen. The lumen wall further includes a second surface which, when combined with the second lumen portion of the interior surface of the lumen wall, forms a second lumen.

As one aspect of the present invention, the cross-sectional areas of the first and second lumens are substantially equal. The lumen wall is shaped so that the first surface of the lumen wall includes a lumen central arcuate portion and two first lumen wing portions located on opposite sides of the first lumen central arcuate portion. The second surface of the lumen wall includes corresponding central arcuate portion and wing portions. As a feature of the present invention, the second lumen arcuate portion is in the shape of a circular arc which is concentric with the first lumen arcuate portion and which has a radius that is 51 to 60 percent of the radius of the second lumen portion of the interior surface. The second lumen central arcuate portion, when combined with a portion of the interior surface of the tubular wall forms a circular guidewire zone in the second lumen which has a radius which is from 50 to 60 percent of the radius of the second lumen portion. This particular shape of the lumen wall allows the use of guidewires which are relatively large with respect to the overall cross-sectional area of the tubular conduit defined by the tubular wall, while at the same time keeping the cross-sectional areas of the first and second lumens substantially equal.

As a feature of the present invention, the exterior surface of the tubular wall may have a circular cross-section which is concentrically located about the interior surface of the tubular wall. In these situations, the kink resistance of the tubing is increased by making the radius of the first lumen portion of the interior wall less than the radius of the second lumen portion to thereby provide a tubular wall having varying thicknesses wherein the thickness of the tubular wall adjacent to the first lumen is greater than the thickness of the tubular wall adjacent to said second lumen. Applicants' arcuate lumen wall design results in a larger circumferential section of the tubular wall being unsupported in the first lumen portion as opposed to the second lumen portion. Accordingly, the increased thickness in lumen wall along the first lumen portion provides increased kink resistance which is specifically applicable to the arcuate lumen wall feature of applicants' invention.

The particular positioning and shape of the lumen wall which in accordance with the present invention provides a dual lumen tubing which is particularly well-suited for use as a dual lumen catheter that has equal lumen cross-sectional areas, relatively large guidewire compatibility and kink resistance.

The above discussed and many other features and attendant advantages of the present invention will become better understood by reference to the following detailed description when taken in conjunction with the accompanying drawings.

DETAILED DESCRIPTION OF THE PREFERRED EMBODIMENT

Figure 1:
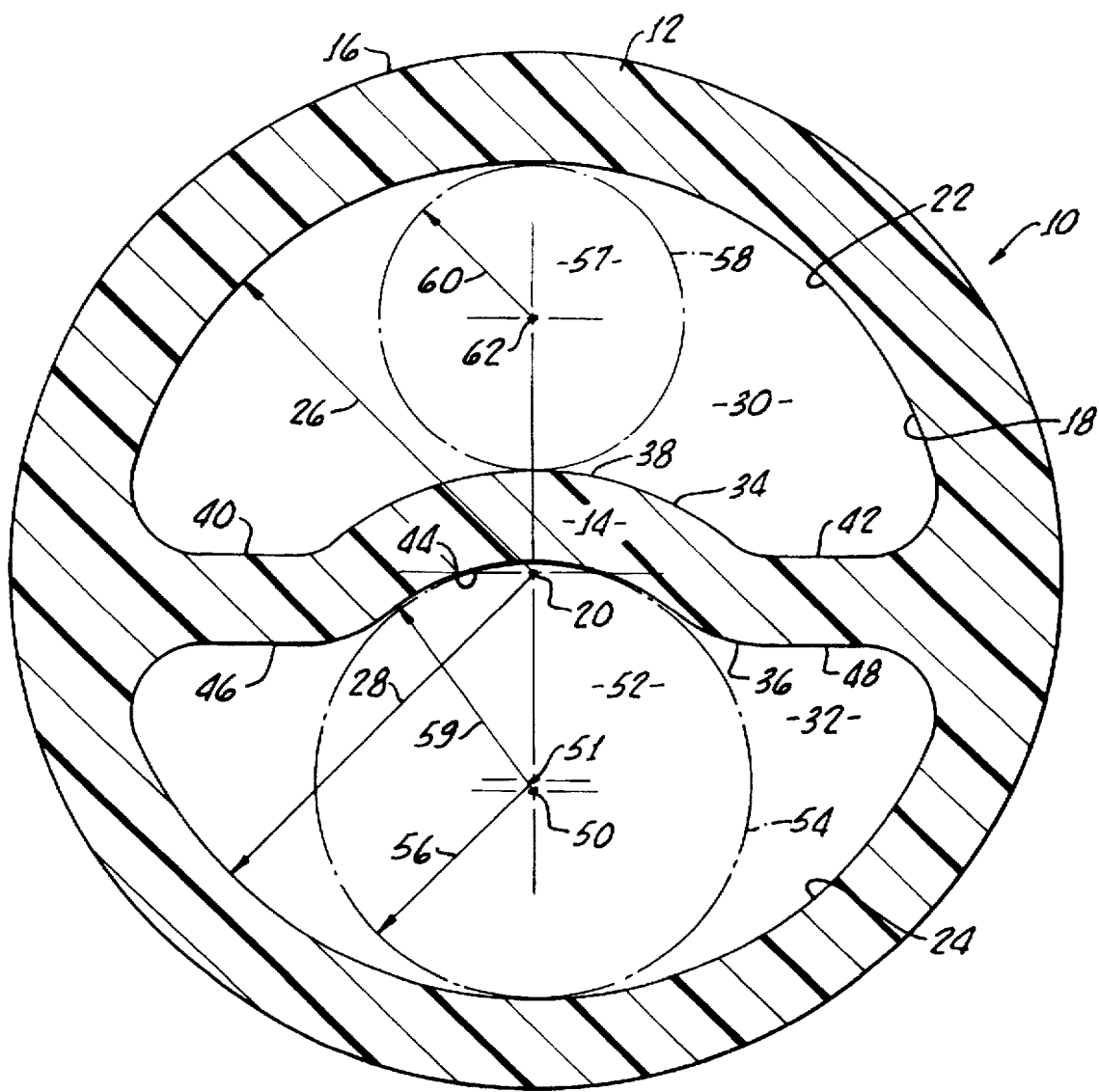
FIG. 1 is a cross-sectional view of a first preferred double lumen tubing in accordance with the present invention.

The double lumen tubing in accordance with the present invention is designed for use as a catheter. The tubing can be used in any catheter application and as part of any catheter device where a dual lumen tubing is required having two lumens with substantially the same cross-sectional area. A first preferred exemplary double lumen tubing in accordance with the present invention is shown generally at 10 in FIG. 1. The double lumen tubing 10 includes a tubular wall 12 and a lumen wall 14. The tubular wall 12 has an exterior surface 16 and an interior surface 18. The interior surface 18 has a circular cross-section located about a longitudinal central axis 20. The interior surface 18 defines a tubular conduit across which the lumen wall 14 extends transversely. The lumen wall 14 also extends parallel to the longitudinal central axis 20. In this preferred embodiment, the exterior surface 16 has a circular cross-section which is concentrically located about the interior surface 18.

The interior surface 18 is divided into a first lumen portion 22 and a second lumen portion 24. The first lumen portion 22 is located along a first lumen radius measured from the longitudinal central axis 20 as represented by segmented arrow 26. The second lumen portion is located along a second lumen radius measured from the longitudinal central axis as represented by segmented arrow 28. As a feature of the present invention, the first lumen portion radius 26 is less than the second lumen radius 28 to provide a tubular wall 12 which has varying thicknesses. Specifically, the thickness of tubular wall 12 adjacent to the first lumen portion 22 is slightly greater than the thickness of the tubular wall 12 adjacent to the second lumen portion 24. This variation in thickness is due to the differences in radiuses 26 and 28. In accordance with the present invention, the stiffness of tubular wall 12 is increased due to this variation in thicknesses. As can be seen from FIG. 1, the circumferential length of first lumen portion 22 is greater than the circumferential length of second lumen portion 24. The slight increase in thickness of tubular wall 12 adjacent to the second lumen portion 22 provides a slight increase in stiffness of this relatively longer unsupported section of the tubular wall 12. The increase in thickness of the tubular wall 12 at the second lumen portion must be kept relatively small so that the requirement of substantially equal lumen cross-sections can be maintained. Increases in wall thickness (variations between radii 26 and 28) are preferably in the range of 0.001 to 0.003 inch. An increase in wall thickness within this range should provide a discernable increase in kink resistance.

The lumen wall 14 is connected to the tubular wall 12 and shaped so as to divide the overall tubular conduit into first and second lumens 30 and 32 which have substantially the same cross-sectional areas. The cross-sectional areas are considered to be substantially the same in accordance with the present invention if their cross-sectional areas are within 15% (fifteen percent) of each other. In addition, the lumen wall 14 is shaped so as to provide a guidewire zone which allows passage of a relatively large guidewire through at least one of the lumens. In the preferred embodiment, the lumen wall 14 is shaped to allow passage of a relatively large guidewire through the second lumen 32.

In order to achieve the above objectives of equal lumen cross-sectional area and large guidewire capabilities, the lumen wall 14 is shaped in the arcuate configuration as shown in FIG. 1. More particularly, the lumen wall 14 has a first surface 34 and a second surface 36. The first surface 34 includes a first lumen central arcuate portion 38 and two first lumen wing portions 40 and 42 located on opposite sides of the first lumen central arcuate portion 38. The second surface 36 of lumen wall 14 also includes a second lumen central arcuate portion 44 and two second lumen wing portions 46 and 48 which are located on opposite sides of the second lumen arcuate portion 44. The first and second lumen central arcuate portions 38 and 44 are in the shape of circular arcs which are concentrically located about an axis 50. In accordance with the present invention, the second lumen central arcuate portion 44 has a radius 59 measured from axis 50 which is equal to 50 to 60 percent of the radius 28 of the second lumen portion interior surface 24. The second lumen central arcuate portion 44, in combination with the second lumen portion 24, defines a circular guidewire zone 52 which is depicted by the phantom circular line 54 in FIG. 1. The radius of the guidewire zone 52 about axis 51 is depicted by segmented arrow 56. It should be noted that the center axis 51 of the circular guidewire zone 52 does not fall exactly at the center axis 50 for the lumen wall concentric arcuate portions 38 and 44. The preferred radius 56 for the guidewire zone 52 is about 52 percent of the radius 28 for the second lumen portion 24 of interior surface 18.

In addition to accepting guidewires through guidewire zone 52, the double lumen tubing 10 in accordance with the present invention can also receive guidewires through the first lumen 30. Guidewires passed through lumen 30 must necessarily have a smaller radius than guidewires passed through guidewire zone 52. The location through which guidewires may be passed in lumen 30 is shown as guidewire zone 57. The circular border of guidewire zone 57 is depicted by circular phantom line 58 which has a radius 60 about axis 62.

The double lumen tubing 10 is suitable for use in a wide variety of situations where a dual lumen catheter having two lumens with substantially equal cross-sectional areas are required. The unique shape of multi-curved arcuate lumen wall 14 provides two lumens with substantially equal cross-sectional areas which at the same time also allowing the use of relatively-large guidewires in guidewire zone 52 and/or relatively small guidewires in guidewire zone 57. In addition, the use of a relatively smaller radius for the first lumen portion 22 of interior surface 18 increases the thickness of the tubing wall 12 as discussed above to increase the kink resistance of the tubing 10.

Preferred double lumen tubings are those where the cross-sectional area of the first and second lumens is between 0.0010 and 0.0060 square inch. Seven french double lumen tubings having 16/16 gauge individual lumens are preferred. For a seven french double lumen tubing, the cross-sectional areas of the first and second lumens is about 0.0016 square inch. Cross-sectional areas of 0.00174 are also preferred, because this size allows passage of a guidewire of at least 0.035 inch diameter along the lumens. Preferably, the radius 28 of the second lumen portion 24 of interior surface 18 is between about 0.035 and 0.040 inch. It is preferred that the radius 26 of the first lumen portion 22 of interior surface 18 be about 0.001 to 0.003 inch shorter than the radius 28 of the second lumen portion 24.

The approximate dimensions or a preferred exemplary double lumen tubing 10 as shown in FIG. 1 are as follows. The radius of the tubular wall exterior surface 16, as measured from longitudinal central axis 20 is 0.0465 inch. The radius 26 for the first lumen portion 22 of interior surface 18 is 0.0365 inch. The radius 28 of the second lumen portion 24 of interior surface 18 is 0.0375 inch. The radius 59 of the second lumen central arcuate portion 44, as measured from axis 51, is 0.0205 inch. The radius 56 of the guidewire zone 52, as measured from axis 50, is 0.0195 inch. The radius of the first lumen central arcuate portion 38 (as measured from axis 50) is 0.0295 inch. The lumen walls can be made from any of the conventional materials used in making double lumen catheters. Exemplary materials include polyvinyl chloride (PVC), polyurethane, silicone, polyamids, fluoropolymers (e.g. TEFLON), polyolefins (polyethylene, polypropylene), metalocenes, and thermoplastic elastomers. Polyurethane is the preferred material for use in making double lumen tubings in accordance with the present invention.

Figure 2:
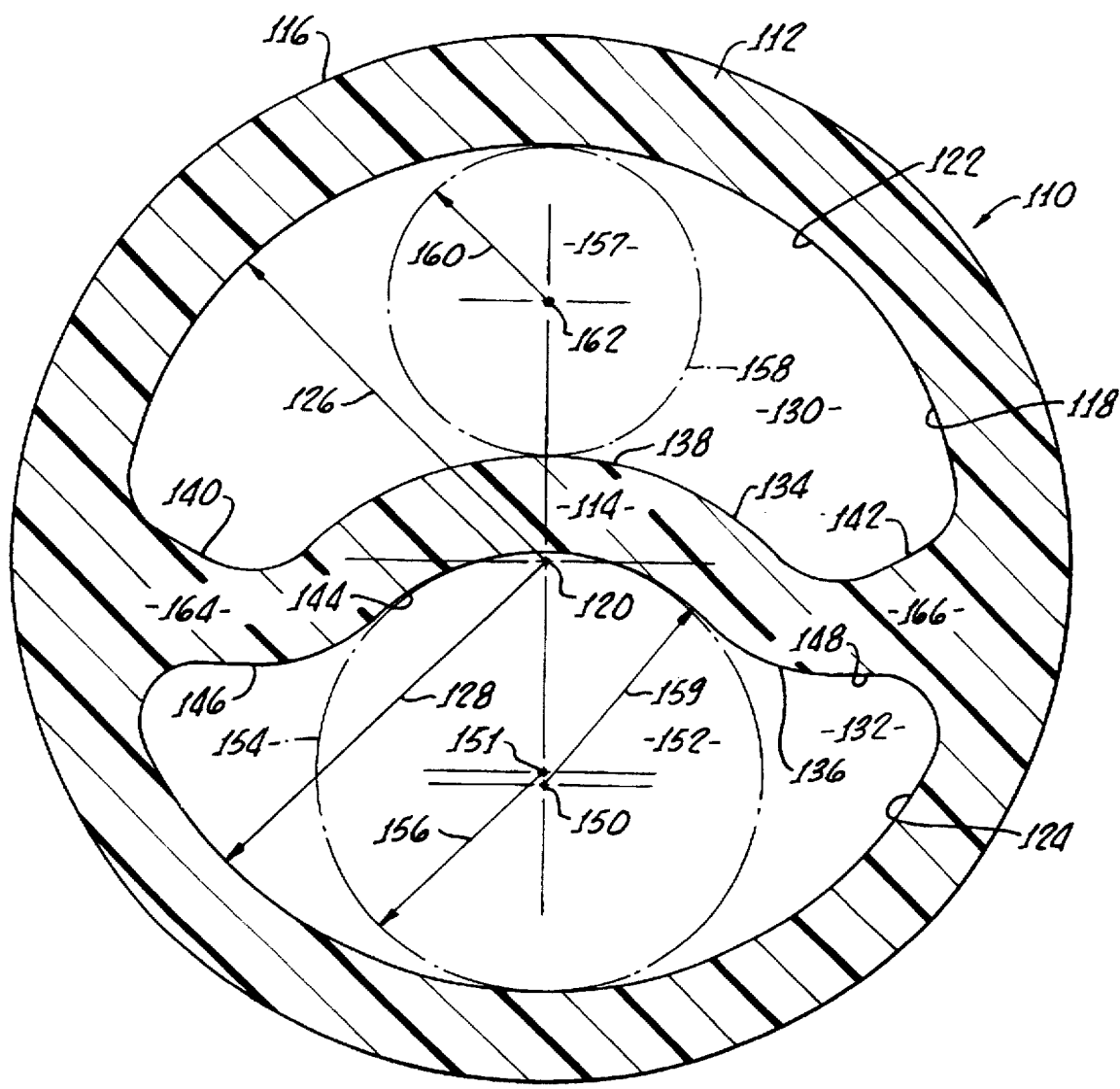
FIG. 2 is a cross-sectional view of a second preferred double lumen tubing in accordance with the present invention.

A second preferred embodiment of the present invention is shown generally at 110 in FIG. 2. The dual lumen tubing 110 is similar to the first tubing embodiment 10 in that both lumens have substantially equal cross-sectional areas and both lumens are capable of receiving the same size large guidewire through one of the lumens. The principal difference between the two embodiments is that the wing portions of the lumen wall in tubing 110 are shaped differently to provide shoulders which are thicker at their attachment point to the tubular wall.

Referring to FIG. 2, the double lumen tubing 110 includes a tubular wall 112 and a lumen wall 114. The tubular wall 112 has an exterior surface 116 and an interior surface 118. The interior surface 118 has a circular cross-section located about a longitudinal central axis 120. The interior surface 118 defines a tubular conduit across which the lumen wall 114 extends transversely. The lumen wall 114 also extends parallel to the longitudinal central axis 120. In this preferred embodiment, the exterior surface 116 has a circular cross-section which is concentrically located about the interior surface 118.

The interior surface 118 is divided into a first lumen portion 122 and a second lumen portion 124. The first lumen portion 122 is located along a first lumen radius measured from the longitudinal central axis 120 as represented by segmented arrow 126. The second lumen portion is located along a second lumen radius measured from the longitudinal central axis as represented by segmented arrow 128. As was the case with the first embodiment, the first lumen portion radius 126 is less than the second lumen radius 128 to provide a tubular wall 112 which has varying thicknesses. Specifically, the thickness of tubular wall 112 adjacent to the first lumen portion 122 is slightly greater than the thickness of the tubular wall 112 adjacent to the second lumen portion 124. This variation in thickness is due to the differences in radiuses 126 and 128. In accordance with the present invention, the stiffness of tubular wall 112 is increased due to this variation in thicknesses. As can be seen from FIG. 2, the circumferential length of first lumen portion 122 is greater than the circumferential length of second lumen portion 124. The slight increase in thickness of tubular wall 112 adjacent to the second lumen portion 122 provides a slight increase in stiffness of this relatively longer unsupported section of the tubular wall.

The lumen wall 114 is connected to the tubular wall 112 and shaped so as to divide the overall tubular conduit into first and second lumens 130 and 132 which have substantially the same cross-sectional areas. In addition, the lumen wall 114 is shaped so as to provide a guidewire zone which allows passage of a relatively large guidewire through at least one of the lumens. In the preferred embodiment, the lumen wall 1 14 is shaped to allow passage of a relatively large guidewire through the second lumen 132.

In order to achieve the above objectives of equal lumen cross-sectional area and large guidewire capabilities, the lumen wall 114 is shaped in the arcuate configuration as shown in FIG. 2. More particularly, the lumen wall 114 has a first surface 134 and a second surface 136. The first surface 134 includes a first lumen central arcuate portion 138 and two first lumen wing portions 140 and 142 located on opposite sides of the first lumen central arcuate portion 138. The second surface 136 of lumen wall 114 also includes a second lumen central arcuate portion 144 and two second lumen wing portions 146 and 148 which are located on opposite sides of the second lumen arcuate portion 144. The first and second lumen central arcuate portions 138 and 144 are in the shape of circular arcs which are concentrically located about a central axis 150. In accordance with the present invention, the second lumen central arcuate portion 144 has a radius 159 measured from axis 150 which is equal to 50 to 60 percent of the radius 128 of the second lumen portion interior surface 124. The second lumen central arcuate portion 144, in combination with second lumen portion 124, defines a circular guidewire zone 1 52 which is depicted by the phantom circular line 154 in FIG. 2. The radius 156 of the guidewire zone 152, as measured from central axis 151, and by second lumen portion 124, is depicted by segmented arrow 156. The preferred radius 156 for the guidewire zone 152 is about 52 percent of the radius 128 for the second lumen portion 124 of interior surface 118.

In addition to accepting guidewires through guidewire zone 152, the double lumen tubing 110 in accordance with the present invention can also receive guidewires through the first lumen 130. Guidewires passed through lumen 130 must necessarily have a smaller radius than guidewires passed through guidewire zone 152. The location through which guidewires may be passed in lumen 130 is shown as guidewire zone 157. The circular border of guidewire zone 157 is depicted by circular phantom line 158 which has a radius 160 about axis 162.

The double lumen tubing 110 is suitable for use in a wide variety of situations where a dual lumen catheter having two lumens with substantially equal cross-sectional areas are required. The unique shape of multi-curved arcuate lumen wall 114 provides two lumens with substantially equal cross-sectional areas which also allowing the use of relatively-large guidewires in guidewire zone 152 and/or relatively small guidewires in guidewire zone 157. In addition, the use of a relatively smaller radius for the first lumen portion of interior surface 118 increases the thickness of the tubing wall 112 as discussed above to increase the kink resistance of the tubing 110. In addition, the lumen wall 114 is shaped to provide transition shoulders 164 and 166 between the lumen wall 114 and tubular wall 112 which are thicker than the lumen wall 114. These transition shoulders 164 and 166 provide additional reinforcement for tubing 110 which increases the stiffness and resistance to kinking of the tubing. The approximate dimensions for this second embodiment are the same as those set forth for the first embodiment (FIG. 1).

The double lumens in accordance with the present invention utilize in an optimized fashion the available area of the tubular cross-section of the overall lumen to provide maximum lumen areas for flow, and the required walls to provide a structure that is sufficiently kink resistant, without wasting any additional area. This double lumen configuration provides the maximum possible flow rates for the two lumens with a minimum risk that the tube will kink and restrict the flow of fluid.

Having thus described exemplary embodiments of the present invention, it should be noted by those skilled in the art that the disclosures herein are exemplary only and that various other alternations, adaptations and modifications may be made within the scope of the present invention. Accordingly, the present invention is not limited to the specific embodiments as illustrated herein.

What is claimed is:

1. A double lumen tubing adapted for use as a catheter, said double lumen tubing comprising:

a tubular wall comprising an exterior surface and an interior surface, said interior surface having a circular cross-section located about a longitudinal central axis which defines a tubular conduit, said interior surface comprising a first lumen portion located along a first lumen radius measured from said longitudinal central axis and a second lumen portion located along a second lumen radius measured from said longitudinal central axis;

a lumen wall extending parallel to said longitudinal central axis and extending transversely across said tubular conduit between spaced locations on said interior surface, said lumen wall comprising a first surface which, when combined with said first lumen portion of said interior surface, defines a first lumen, said first lumen having a cross-sectional area, said lumen wall further comprising a second surface which, when combined with said second lumen portion of said interior surface, defines a second lumen, said second lumen having a cross-sectional area, wherein the cross-sectional areas of said first and second lumens are substantially equal, said first surface of said lumen wall having a first lumen central arcuate portion and two first lumen wing portions located on opposite sides of said first lumen central arcuate portion, said second surface of said lumen wall having a second lumen central arcuate portion and two second lumen wing portions located on opposite sides of said second lumen arcuate portion, wherein said second lumen arcuate portion is in the shape of a circular arc which is concentric with said first lumen arcuate portion and which has a radius that is from 50 to 60 percent of the radius of said second lumen portion of said interior surface to thereby form a circular guide wire zone in said second lumen which has a radius of from 50 to 60 percent of the radius of said second lumen portion and which is bordered on one side by said second lumen arcuate portion and bordered on the other side by said second lumen portion of said interior surface.

2. A double lumen tubing according to claim 1 wherein said exterior surface has a circular cross-section concentrically located about said interior surface and wherein the radius of said first lumen portion is less than the radius of said second lumen portion to thereby provide a tubular wall having varying thicknesses wherein the thickness of said tubular wall adjacent to said first lumen is greater than the thickness of said tubular wall adjacent to said second lumen.

3. A double lumen tubing according to claim 1 wherein said second lumen arcuate portion is in the shape of a circular arc which has a radius that is about 52 percent of the radius of said second lumen portion of said interior surface to thereby form a circular guide wire zone in said second lumen which has a radius of about 52 percent of the radius of said second lumen portion of said interior surface.

4. A double lumen tubing according to claim 2 wherein said second lumen arcuate portion is in the shape of a circular arc which has a radius that is about 52 percent of the radius of said second lumen portion of said interior surface to thereby form a circular guide wire zone in said second lumen which has a radius of about 52 percent of the radius of said second lumen portion of said interior surface.

5. A double lumen tubing according to claim 1 wherein the cross-sectional area of said first and second lumens is between 0.0010 and 0.0060 square inch.

6. A double lumen tubing according to claim 2 wherein the cross-sectional area of said first and second lumens is between 0.0010 and 0.0060 square inch.

7. A double lumen tubing according to claim 1 wherein the cross-sectional area of said first and second lumens is about 0.00174 square inch.

8. A double lumen tubing according to claim 2 wherein the cross-sectional area of said first and second lumens is about 0.00174 square inch.

9. A double lumen tubing according to claim 1 wherein the radius of said second lumen portion of said interior surface is between about 0.035 and 0.040 inch.

10. A double lumen tubing according to claim 9 wherein the radius of said first lumen portion of said interior surface is about 0.001 to 0.003 inch larger than the radius of said second lumen portion.

11. A guide wire introduction system comprising a double lumen tubing according to claim 1 and a guide wire located within said guide wire zone of said second lumen.

12. A guide wire introduction system comprising a double lumen tubing according to claim 2 and a guide wire located within said guide wire zone of said second lumen.

13. A guide wire introduction system comprising a double lumen tubing according to claim 1 and a guide wire located within said first lumen.

14. A guide wire introduction system comprising a double lumen tubing according to claim 2 and a guide wire located within said first lumen.

15. A guide wire introduction system according to claim 11 wherein a second guide wire is located within said first lumen.

16. A guide wire introduction system according to claim 12 wherein a second guide wire is located within said first lumen.

* * * * *